United States Patent [19]

Fleischhacker et al.

[11] 3,973,556

[45] Aug. 10, 1976

[54] SMOOTHENED COIL SPRING WIRE GUIDE

[75] Inventors: John J. Fleischhacker; Joseph F. Fleischhacker, Jr., both of Minnetonka, Minn.

[73] Assignee: Lake Region Manufacturing Company, Inc., Chaska, Minn.

[22] Filed: June 20, 1975

[21] Appl. No.: 588,793

[52] U.S. Cl. ............................ 128/2 M; 128/2.05 R; 128/DIG. 9; 128/348; 267/180
[51] Int. Cl.² .................................... A61M 25/00
[58] Field of Search ......... 128/2 M, 2.05 R, DIG. 9, 128/348; 267/180, 166

[56] References Cited
UNITED STATES PATENTS

| | | | |
|---|---|---|---|
| 2,118,631 | 5/1938 | Wappler | 128/2 M X |
| 2,622,448 | 12/1952 | Lorig | 267/180 X |
| 3,452,742 | 7/1969 | Muller | 128/2 M |
| 3,521,620 | 7/1970 | Cook | 128/2.05 |
| 3,528,406 | 9/1970 | Jeckel et al. | 128/2.05 |
| 3,547,103 | 12/1970 | Cook | 128/2.05 |
| 3,727,902 | 4/1973 | Burckhardt et al. | 267/180 |
| 3,841,308 | 10/1974 | Tate | 128/2 M |

*Primary Examiner*—Kyle L. Howell
*Attorney, Agent, or Firm*—Dugger, Johnson & Westman

[57] ABSTRACT

A coil spring guide, for use in connection with the insertion of a catheter into the vessels of a body, that has a coil spring, and a wire core extending within the coil spring and having a distal end welded to the distal end of the coil spring. The coil spring is made from metal wire that in a straightened condition is circular in transverse cross section throughout its length, and that after being coiled, to have adjacent helics abut against one another. Thereafter the radially outer circumferential portion of the coil is ground away to provide a helical radially outer spring coil surface (chordal surface) that is of a substantially constant radius throughout the axial length of the coiled wire and has a helix width of a chord parallel to the central longitudinal axis of the coil spring that is subtended by about a 10°–140° angle of two radii of the coil spring wire. Advantageously, prior to carrying out a material removal step on the coil spring to provide the helical chordal surface, the surface of the coil spring radially outwardly of the coil helics in abutting relationship is coated with a plastic material and the plastic coating is removed during the material removal except for any part of the coating that does not extend further radially outward of the coil spring central axis than the chordal surface; or alternately the coil spring may be coated with the plastic coating after the material removal step to provide a coating covering the helical chordal surface.

9 Claims, 8 Drawing Figures

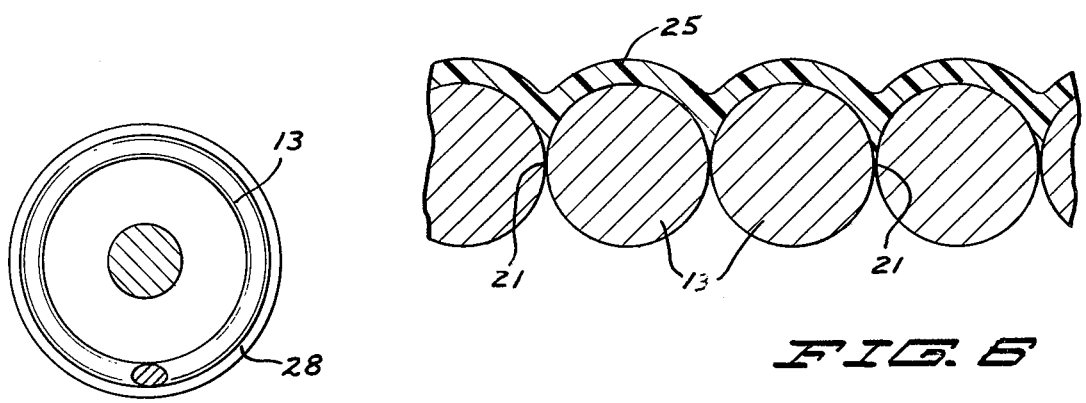
FIG. 7
FIG. 6
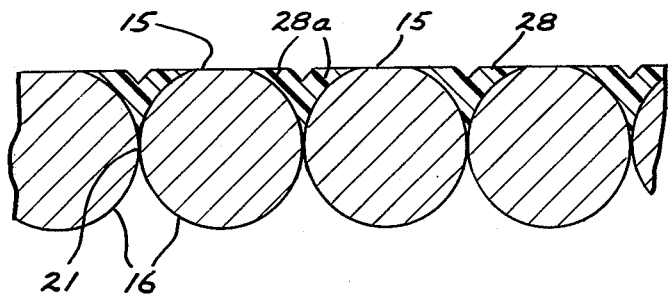
FIG. 8

3,973,556

SMOOTHENED COIL SPRING WIRE GUIDE

BACKGROUND OF THE INVENTION

A coil spring guide for use in connection with the insertion of catheters into the vessels of a body. Most prior art have circumferentially rounded, outer surfaces that extend more remote from the center axis of the coil spring than the remainder of the guide. These rounded surfaces together with the interstices between the rounded surfaces of adjacent helics, provide a roughened surface that is engageable with the vessels and causes irritation and induces trauma in the vessels as the guide is moved therein, which is undesirable. Another spring coil is formed from a long strip of metal that is rectangular in transverse cross section. However, as a particular matter, when coiling such strips, the coiled strip in transverse cross section forms a concave helical recess extending the length of the strip opening radially outwardly. Grinding or burnishing the outer surface of such a coiled strip to have an outer surface of a substantially round cylindrical configuration could result in the adjacent edges of adjacent helics being sharpened, which when the guide is bent, can scrape against the wall of a vessel. Again, such is undesirable. Further, spring coils of such strips do not have as desirable bending characteristics in going around curves in vessels of the body as spring coils of a circular cylindrical wire as adjacent helics of such strips on one side of the coil have to spread further for a guide of substantially the same strength and outer diameter. In order to minimize or overcome problems such as the above, as well as others, this invention has been made.

SUMMARY OF THE INVENTION

A coil spring guide having a wire core and a coil spring having the wire core extended therein and secured thereto, the coil spring having a helical, chordal, radially outer surface while the remainder of the wire forming the coil spring is generally circular. Preferably the outer surfaces of coil spring in the radially outer interstices of the coil spring between adjacent helics may be covered with a coating that does not extend substantially further outward of the central coil axis than the chordal surfaces, or that does extend outward to cover such chordal surfaces.

BRIEF DESCRIPTION OF THE DRAWINGS

FIG. 6 is an enlarged, fragmentary, longitudinal cross sectional view of the coil spring of FIG. 1 that has been coated to illustrate a step in forming the third embodiment of the invention;

FIG. 7 is a transverse cross sectional view of the guide of FIG. 6, the radial thickness of the coating relative to the wire of the coil being exaggerated to facilitate the illustration thereof; and FIG. 8 is a fragmentary longitudinal view through the coil spring wire of FIG. 6 after it has been ground to provide the coil spring guide of the third embodiment of the invention that has a chordal surface.

Referring now to FIGS. 1 and 2, the coil spring guide thereof includes a tightly wound coil spring 12 that in a straight condition, has adjacent helics abutting. The spring 12 may be of any length, but usually is 80 cm. to 150 cm., or longer, and preferably is made of stainless steel or other alloys that are non-corrosive when used in the body. The outside diameter of the coil is usually about 0.018 inch to 0.045 inch, while the diameter of the wire of the coil spring prior to providing the chordal surface to be described usually is in the range of 0.010 inch to 0.004 inch. The coil spring is preferably made of stainless steel. Extending within the coil spring is a wire core 11. The wire core, which is preferably of stainless steel, includes a distal end portion that is welded to the distal end of the coil spring at 14. Insofar as the present invention is concerned the construction of the wire core may be varied, and more than one wire core may be provided in the coil spring.

Figure 1:
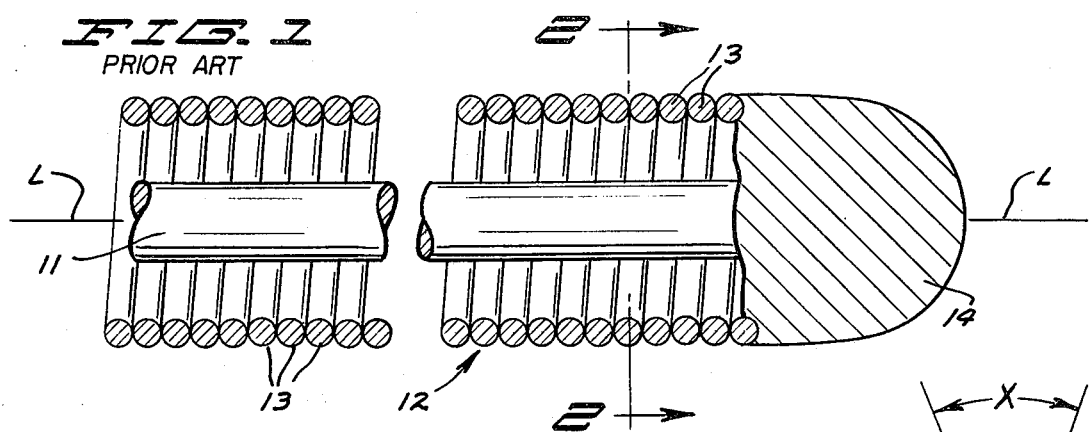
FIG. 1 is a longitudinal cross sectional view, generally taken along the line and in the direction of the arrows 1—1 of FIG. 2 of a prior art coil spring guide in a straightened condition, the spring coil being of circular cylindrical wire, and the proximal end portion and a longitudinally intermediate part of the guide not being shown.
Figure 3:
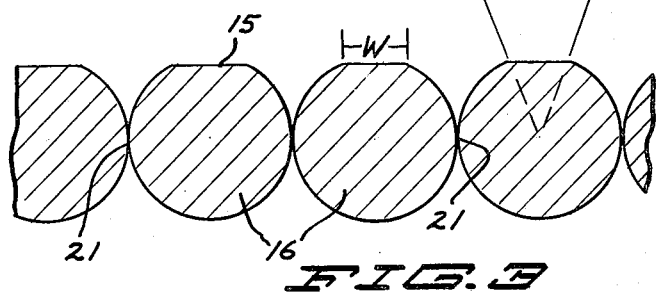
FIG. 3 is an enlarged, fragmentary, longitudinal cross sectional view of a coil spring of the first embodiment of the invention on one side of the central axis of the coil spring, the wire of the coil spring having been ground to form the chordal surface.
Figure 2:
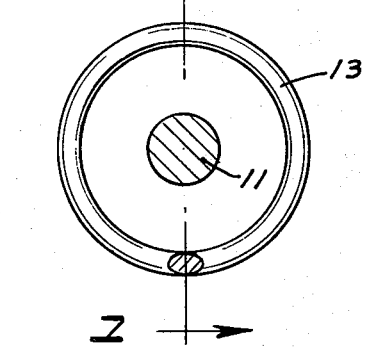
FIG. 2 is transverse cross sectional view of the prior art guide that is generally taken along the line and in the direction of the arrows 2—2 of FIG. 1.

Adjacent helics 13 of the coil spring in a straight relaxed condition such as indicated in FIGS. 1 and 3 abut against one another throughout substantially the entire circumference of the helics (helical line contact with one another at diametrically opposite sides at 21). In order to provide the first embodiment of FIG. 3 from the guide of FIG. 1, each helix 13 of the part of the coil spring to be extended into a vessel is formed to have a chordal radial outer surface 15 that is parallel to the central axis L—L of the coil spring in a coil spring straightened, relaxed condition and extends completely circumferentially around the helix 16. The width W of the chordal surface of each helix 16 is substantially less than the diameter of the wire forming the helix that is parallel to the central axis L—L, and the width W is that of a chord of the wire that is subtended by about an angle X of two radii of the coil spring wire, that lie in a plane of the central axis L—L. Desirably the angle X is about 10°–140°, more desirably about 10°–60°, and preferably about 60°. As a result, the cross sectional area of the coil spring wire and accordingly the strength thereof is decreased only slightly, whereas, the area of the surface (chordal surface) of each helix radially furthest remote from the central axis of the coil spring is substantially increased from that of a coil spring made of wire that is circular throughout the length thereof. In this connection, the chordal surfaces 15 of each helix are substantially coextensive (but axially spaced) with a common circular cylindrical surface that extends the axial length of the coil spring in a straightened, relaxed condition.

Figure 4:
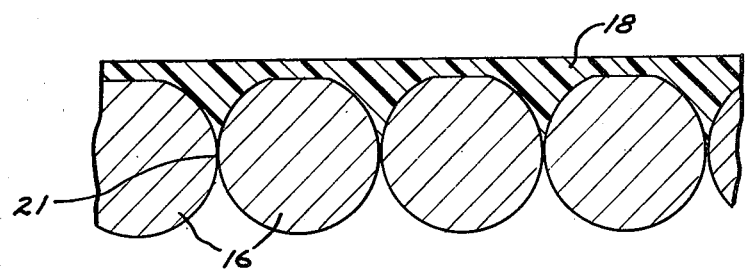
FIG. 4 is a view similar to that of FIG. 3 except that the radially outer surface of the coil spring of FIG. 3, including the chordal surface, has been coated to form the second embodiment of the invention, the thickness of the coating being exaggerated.

The coil spring of FIG. 3 may be used without a coating referred to below and has advantages over that of the coil of FIG. 1 in that less trauma to the body vessels results from the use thereof than from the use of the guide of FIG. 1. However, the coil spring of FIG. 3 may be provided with a coating 18 of Teflon or other plastic material having similar properties, that is adhered to the radially outer surface of the coil spring to have a circular cylindrical outer surface to provide the second embodiment of FIG. 4. That is, coating 18 not only fills the interstices of adjacent helics radially outwardly of the abutting parts 21 of the helics 16 in a coil spring straightened condition, but also covers the chordal surfaces 15.

Alternately there may be provided a spring guide of the third embodiment of the invention of FIG. 8. In making the spring guide of FIG. 8, advantageously a wire that is circular in cross section through its length is tightly wound to form a coil spring of substantial constant outer coil diameter, and wire core is mounted in the coil spring as shown in FIG. 1. Thence the entire radially outer surface of the coil spring is Teflon coated as is in part indicated at 25 in FIG. 6. Thereafter the outer surface portion of the coated coil spring is removed, for example, by grinding, to provide helics 16 having the chordal surface 15 and the coating 28 in the helical interstices that has co-circular cylindrical extension surfaces 28a axially on either side of each helical chordal surface 15. If the initial coating is of a sufficient radial thickness relative the coil spring central axis, then after material removal, the radially outer surface of the coating would extend axially completely across the gap between adjacent helical chord surfaces 15 and co-circular cylindrical therewith to have surfaces 15 uncoated; while if the coating was of a small thickness, the coating would have a concaved recessed outer surface portion between axially adjacent coating surfaces 28a of axially adjacent pairs of helics 16 such as indicated in FIG. 8.

That is, coating 28 is adhered on the radially outer surface of the coil spring of FIG. 8, but does not extend radially outwardly of the central axis of the coil spring substantially further than the chordal surfaces 15, nor cover the chordal surfaces 15. Thus the surfaces of adjacent helics in the coil spring radially outward interstices bounded by a circular cylinder surface extending axially between and co-cylindrical with adjacent pair of helics chordal surfaces 15 and the arcuate surfaces of the adjacent pair of helics that are radially between the intersection thereof with the last mentioned circular cylinder and the location 21 that the helics abut against one another, are covered by an integral coat of Teflon 28.

Figure 5:
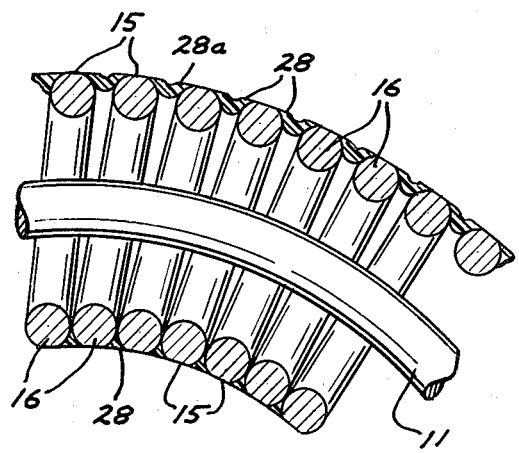
FIG. 5 is a fragmentary longitudinal view through the coil spring guide of FIG. 8 that is being bent to indicate the coating forms a seal between adjacent helics of the coil spring of the third embodiment of the invention.

The coil spring guide of this invention may be used without a plastic coating thereon (first embodiment), and if it does not have the coating, the guide still results in substantially less irritation and trauma to blood vessels than when wire guides are used with a coil spring that is of circular cylindrical wire. Advantageously the coil spring having the wire chordal surfaces is Teflon coated as described herein. Without the coating, even though the coil spring is tightly wound, when the coil spring is bent, the axially adjacent helics on one diametric side of the coil spring remain in abutting contact while the remainder of the helics separate, for example such as indicated in FIG. 5. As a result, without the coating, body liquids and particulate material can enter between the helics and be trapped in the coil spring, and as a practical matter such material cannot be completely removed. In the event the coil spring guide is thereafter inserted in the vessel of another patient, when the spring guide is bent, the trapped material from the first patient can escape into the vessel of the second patient, which is undesirable. However with the coating described, even though during bending, substantial portions of adjacent wire helics are out of abutting relationship to one another, due to the coating extending between and adhering to adjacent wire helics, and the resiliency or stretchability of the coating, the coating tends to form a fluid seal between adjacent wire helics to minimize or prevent body liquids and other material entering therebetween, even if the coil spring guide is arcuately bent through a substantial angle. Additionally, the coated wire guide provides lubricity so that the plastic catheter slides over the guide more easily to the desired position than it would slide over a non-coated wire guide and does substantially decrease the size of, if not eliminate (fills in), the radially outer open interstices between adjacent wire helics; the second embodiment eliminating said interstices and providing more efficient use of urethane type catheters. In the second embodiment, due to providing chordal surfaces 15, the outer diameter of the coated helics can be maintained while using a larger diameter wire than possible if the chordal surfaces were not provided.

Inasmuch as the use of wire guides has been described in the prior art, for example, U.S. Pat. No. 3,528,406, Col. 1, lines 20–38, a more detailed description of the use of the wire guide of this invention is not believed necessary and will not be set forth.

What is claimed is:

1. A vascular coil spring guide comprising an elongated coil spring having a central axis and an elongated distal end portion, and an elongated wire core extending within said distal end portion, said distal end portion including adjacent wire helics that in coil spring straightened condition have helical chordal surfaces substantially parallel to said central axis and of substantially the same radial spacing from said central axis throughout the helical circumferential length thereof, and partial, substantially circular cylindrical helical surfaces having radii of curvature emanating from the helics axis of helical curvature of the helics about said central axis.

2. The coil spring guide of claim 1 further characterized in that the chordal surface of each of the helics is of a width parallel to central axis that is subtended by about 10°–140° angle of two radii of the cylindrical surface part of the coil spring wire that are in a plane of the central axis of the coil spring.

3. The spring guide of claim 2 further characterized in that said angle is about 60°. coil spring, 4. The coil spring guide of claim 1 further characterized in that the wire helics are of metal, and that in a coil spring straightened condition, adjacent helics are in axial abutting relationship a substantial distance radially inwardly of the chordal surfaces.

5. The coil spring guide of claim 1 further characterized in that there is provided a plastic coating that is adhered to the coilspring, extending between adjacent helics, including said chordal surfaces thereof, and having an outer surface between chordal surfaces of adjacent helics that extends radially outward of said central axis in a coil spring straightened condition.

6. The coil spring guide of claim 5 further characterized in that said coating has a substantially circular cylindrical radially outer surface, said coating covering said chordal surfaces.

7. The coil spring guide of claim 5 further characterized that said coating extends a maximum distance from the central axis substantially the same as the radial spacing of the chordal surfaces from the central axis, said chordal surfaces being substantially free of said coating.

8. The spring guide of claim 7 further characterized in that in a coil spring straightened condition, the axially adjacent wire helics are in abutting relationship to form radially outer interstices and the coating radially outer surface has surface portions forming a substantially co-circular cylindrical extension of the chordal surfaces of adjacent helics, and that the coating is adhered to the adjacent helics surfaces of said interstices thereof radially between the chordal surfaces and the abutting parts of the wire helics.

9. A vascular coil spring guide comprising an axially elongated spring metal coil spring having a central axis and an elongated wire core extending within said coil spring and secured thereto, said coil spring in a coil straightened condition having axially adjacent wire helics in abutting relationship at a substantial constant radial distance from the central axis, said helics having chordal surfaces of substantial axial width that are radially outwardly of the locations the helics abut against one another and are of substantially the same radii of curvature throughout their axial width and helical circumferential length, each helics in cross section on opposite sides of said central axis in a plane of central axis being circularly curved radially inwardly of the intersection of said plane with the respective chordal surface of the respective helix.

* * * * *

UNITED STATES PATENT AND TRADEMARK OFFICE
CERTIFICATE OF CORRECTION

PATENT NO. : 3,973,556
DATED : August 10, 1976
INVENTOR(S) : John J. Fleischhacker; Joseph F. Fleischhacker, Jr.

It is certified that error appears in the above-identified patent and that said Letters Patent are hereby corrected as shown below:

Column 4, line 3 (Claim 3, line 2) remove "coil spring,".

Signed and Sealed this

Twenty-sixth Day of October 1976

[SEAL]

Attest:

RUTH C. MASON
*Attesting Officer*

C. MARSHALL DANN
*Commissioner of Patents and Trademarks*